US006183694B1

(12) United States Patent
Radtke et al.

(10) Patent No.: US 6,183,694 B1
(45) Date of Patent: Feb. 6, 2001

(54) SPECTROPHOTOMETRIC APPARATUS FOR REDUCING FLUID CARRYOVER

(75) Inventors: Marilyn Radtke, South Bend; Gary E. Rehm, Elkhart, both of IN (US)

(73) Assignee: Bayer Corporation, Elkhart, IN (US)

( * ) Notice: Under 35 U.S.C. 154(b), the term of this patent shall be extended for 0 days.

(21) Appl. No.: 09/182,313

(22) Filed: Oct. 30, 1998

(51) Int. Cl.[7] ................................................. G01N 35/04
(52) U.S. Cl. ............................... 422/65; 422/63; 422/66; 422/82.05
(58) Field of Search ................................. 422/63, 66, 65, 422/67, 82.05, 82.08; 436/43, 44, 46, 47, 48

(56) References Cited

U.S. PATENT DOCUMENTS

| | | | |
|---|---|---|---|
| 4,689,202 | 8/1987 | Khoja et al. | 422/65 |
| 4,820,491 | 4/1989 | Khoja et al. | 422/63 |
| 5,055,261 | 10/1991 | Khoja et al. | 422/64 |
| 5,143,694 | * 9/1992 | Schafer et al. | 422/65 |
| 5,654,803 | * 8/1997 | Howard, III et al. | 356/446 |
| 5,686,047 | * 11/1997 | Augstein | 422/65 |

FOREIGN PATENT DOCUMENTS

0997715 * 5/2000 (EP) .

* cited by examiner

*Primary Examiner*—Jeffrey Snay
(74) *Attorney, Agent, or Firm*—Jerome L. Jeffers (57) ABSTRACT

An apparatus adapted to inspect reagent strips having fluid samples, such as urine samples, disposed thereon and to reduce the likelihood of contamination of one of the fluid samples with another of the fluid samples is provided with a reagent strip support (22) adapted to support a reagent strip (14) having a plurality of reagent pads (26) disposed in a longitudinal direction along the reagent strip (26), including reagent pad which has a reagent sensitive to contamination. The apparatus also includes a reagent strip mover (18 and/or 80) adapted to cause the reagent strip (14) to be moved in a direction generally transverse to the longitudinal direction from an initial reagent strip location to an inspection location (120 or 122), a light emitter (64 or 68) adapted to illuminate the reagent strip (14) when the reagent strip (14) is supported by the reagent strip support (18 and/or 80) at the inspection location (120 or 122), and a detector (66 or 70) adapted to receive light from the reagent strip (14) when the reagent strip (14) is being illuminated by the light emitter (64 or 68).

17 Claims, 6 Drawing Sheets

SPECTROPHOTOMETRIC APPARATUS FOR REDUCING FLUID CARRYOVER

BACKGROUND OF THE INVENTION

The present invention relates to an apparatus for performing optical inspection tests on reagent strips having samples of body fluid thereon which reduces the likelihood of carryover of body fluid from one reagent strip to another.

Conventional spectrophotometers may be used to perform a number of different urinalysis tests utilizing a reagent strip on which a number of different reagent pads are disposed. Each reagent pad may be provided with a different reagent which causes a color change in response to the presence of a certain type of constituent in urine, such as leukocytes (white blood cells) or erythrocytes (red blood cells). The color change is detected by the spectrophotometer by illuminating the pad and taking a number of reflectance readings from the pad, each having a magnitude relating to a different wavelength of light. The color may then be determined based upon the relative magnitudes of red, green and blue reflectance signals, for example.

In a conventional spectrophotometer, the process of inspecting a reagent strip is performed by dipping the reagent strip in a urine sample, blotting excess urine from the reagent strip, placing the reagent strip at a designated location in the spectrophotometer, and pressing a start button which causes the spectrophotometer to begin automatic processing and inspection of the reagent strip.

Figure 1:
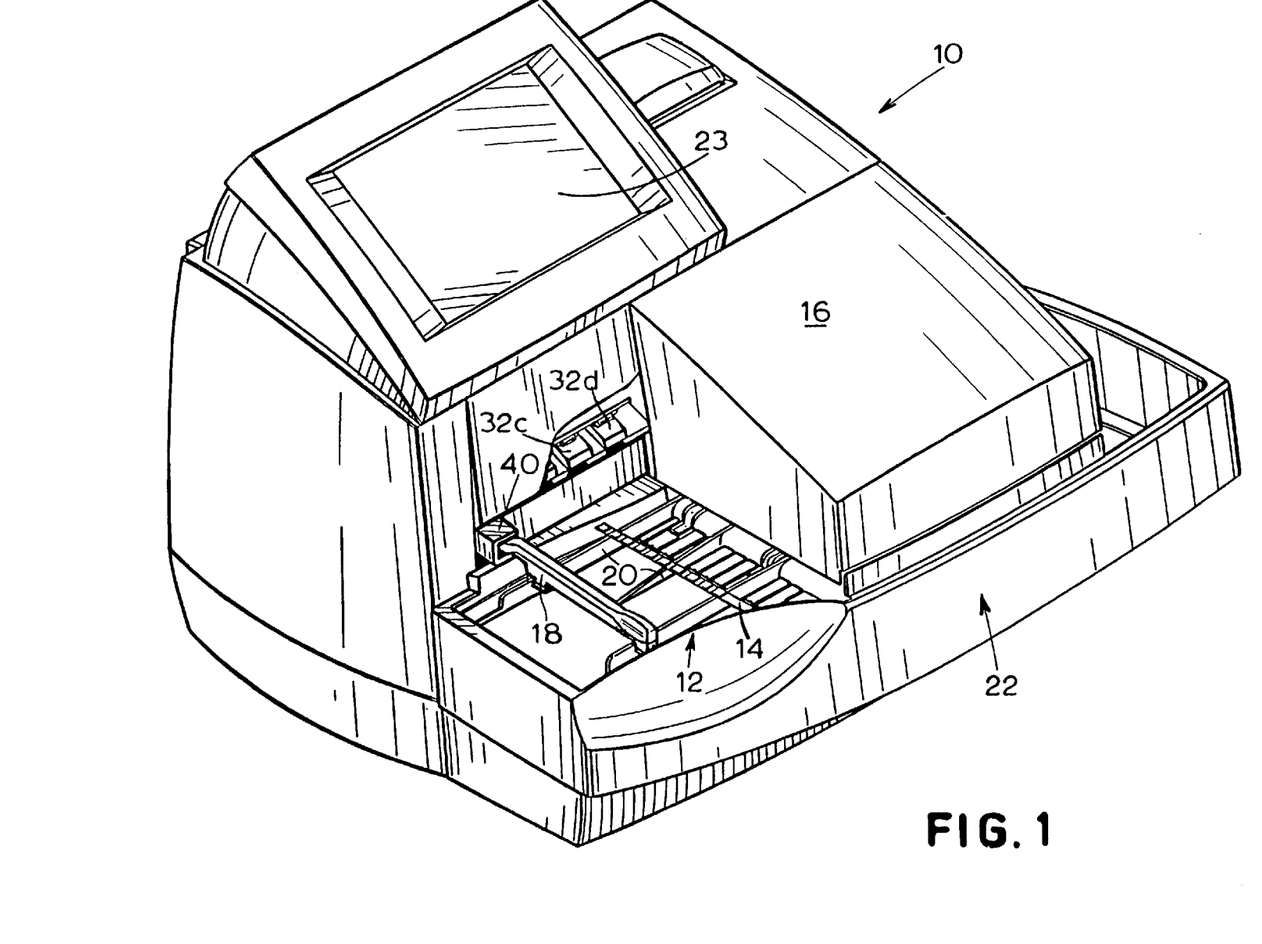
FIG. 1 is a perspective view of a spectrophotometer which may be used to perform various tests of a body fluid sample disposed on a reagent strip.
Figures 1A, 1B:
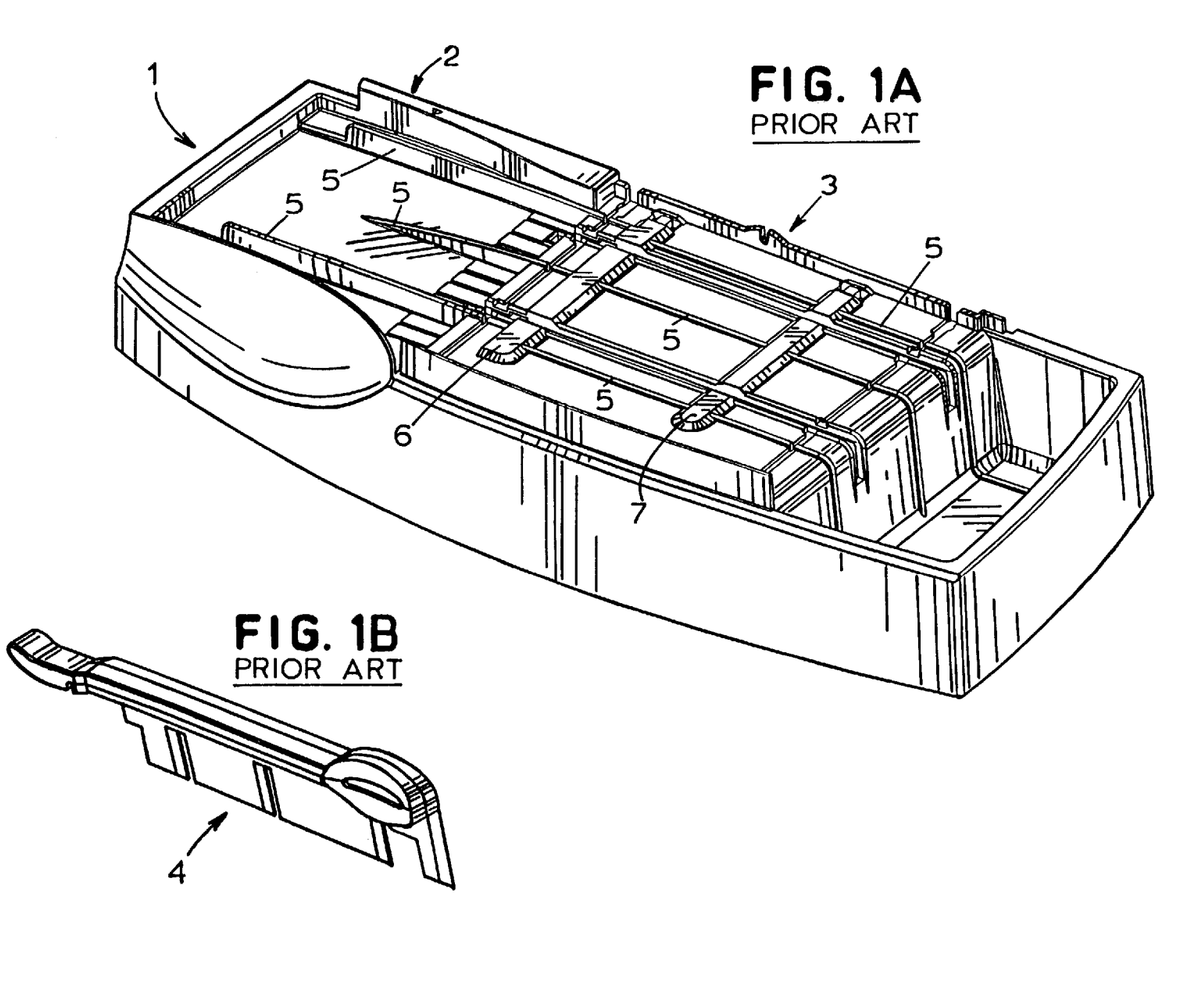
FIG. 1A is a perspective view of a prior art reagent strip support table.
FIG. 1B is a perspective view of a prior art blotter arm adapted to move a reagent strip while the reagent strip is supported by the reagent strip support table shown in FIG. 1A.

FIG. 1A illustrates a prior art table 1 for supporting a reagent strip. The support table 1 has a receiving area 2 on which a reagent strip (not shown in FIG. 1A) is initially placed and an inspection area 3 to which the reagent strip is moved for optical inspection. Reagent strips are moved, one at a time, from the receiving area 2 to the inspection area 3 by a blotter arm 4, shown in FIG. 1B, which makes contact with each reagent strip.

The support table 1 has a plurality of upwardly extending ribs 5 designed to support the reagent strips so that they are held above the upper surfaces of the support table 1. The support table 1 has a first raised platform 6, having the approximate shape of a reagent strip, on which a reagent strip is positioned when being read by a first readhead (not shown), and a second raised platform 7 on which a reagent strip is positioned when being read by a second readhead (not shown).

The blotter arm 4 shown in FIG. 1B was designed to extract or remove urine from a reagent strip when it makes contact with the reagent strip so that significant amounts of urine from one reagent strip will not contaminate, or be left on, the portions of the support tray 1 with which subsequent reagent strips make contact. To that end, the surface of the blotter arm 4 which makes contact with reagent strips is provided with small capillaries (not shown) which draw urine away from the reagent strip due to capillary action.

Other prior art spectrophotometers have been designed to extract urine from reagent strips to prevent fluid carry over from one reagent strip to another. For example, in one prior art spectrophotometer, reagent strips were moved through the device on a paper web which is designed to absorb excess urine from each of the reagent strips.

Conventional reagent strips used in the spectrophotometer having the support table 1 shown in FIG. 1A have multiple reagent pads which are provided with reagents to test for various conditions. One such reagent pad is designed to detect "occult blood" in urine. Such a reagent pad is impregnated with a conventional reagent which causes a blue color to be formed in the presence of very small concentrations of blood in urine.

SUMMARY OF THE INVENTION

The present invention is directed to an apparatus adapted to inspect reagent strips after having body fluid samples, such as urine samples, disposed thereon and to reduce the likelihood of contamination from one body fluid sample with another body fluid sample. The apparatus is provided with a reagent strip support, such as a support table, adapted to support a reagent strip having a plurality of reagent pads disposed in a longitudinal direction along the reagent strip, including, for example, an occult blood reagent pad which has a reagent that enables detection of occult blood. The apparatus also includes a reagent strip mover adapted to cause the reagent strip to be moved in a direction generally transverse to the longitudinal direction from an initial reagent strip location to an inspection location, a light emitter adapted to illuminate the reagent strip when the reagent strip is supported by the reagent strip support at an inspection location, and a detector adapted to receive light from the reagent strip when the reagent strip is being illuminated by the light emitter.

In one aspect of the invention, the reagent strip support and the reagent strip mover are designed not to remove excess body fluid from the reagent strips.

In another aspect of the invention, the occult blood reagent pad is located on the reagent strip at a reagent pad area, and the reagent strip support is adapted to support the reagent strip so that there is no significant physical contact between the reagent strip support and the reagent pad area when the reagent strip is located at the inspection location and when the reagent strip is moved between the initial reagent strip location and the inspection location.

In another aspect of the invention, the reagent strip support is adapted to support the reagent strip so that there is no physical contact between the reagent strip support and a no-contact area when the reagent strip is located at the inspection location and when the reagent strip is moved between the initial reagent strip location and the inspection location, the no-contact area being defined as the combined area of the reagent pad area, a first area extending at least about one-eighth of an inch from the reagent pad area in a first direction parallel to the longitudinal axis of the reagent strip, and a second area extending at least about one-eighth of an inch from the reagent pad area in a second direction parallel to the longitudinal axis of the strip.

The reagent strip mover may be provided with a first portion that makes physical contact with the reagent strip at a first point along the reagent strip and a second portion that makes physical contact with the reagent strip at a second point along the reagent strip, and the reagent pad area of the reagent strip may be disposed between the first and second points along the reagent strip so that the reagent strip mover does not make physical contact with the reagent pad area of the reagent strip.

The reagent strip support may be provided with a first upwardly extending elongated rib which makes physical contact with the reagent strip at a first contact point between the reagent pad area and a first end of the reagent strip and a second upwardly extending elongated rib which makes physical contact with the reagent strip at a second contact point between the reagent pad area and a second end of the reagent strip.

The apparatus may include a reagent strip pusher arm which is adapted to push the reagent strip along the reagent strip support while the reagent strip is being supported by the reagent strip support, the reagent strip pusher arm being shaped so that no portion of the reagent strip pusher arm makes contact with the reagent pad area of the reagent strip.

The features and advantages of the present invention will be apparent to those of ordinary skill in the art in view of the detailed description of the preferred embodiment, which is made with reference to the drawings, a brief description of which is provided below.

DETAILED DESCRIPTION OF THE PREFERRED EMBODIMENTS

FIG. 1 illustrates a spectrophotometer 10 for performing various tests, such as urinalysis tests, on reagent strips. The spectrophotometer 10 has a receiving area 12 at which a reagent strip 14 may be placed and a reagent strip inspection area covered by a housing portion 16. The reagent strip receiving area 12 is located between a laterally movable transfer arm 18 and the left side of the housing portion 16. The reagent strip 14 is supported by a number of relatively thin upwardly extending ribs 20 formed in the left-hand side of a reagent strip support table 22.

To operate the spectrophotometer 10, the reagent strip 14 is placed in the receiving area 12. The spectrophotometer 10 may be designed to automatically detect the presence of the reagent strip 14, and upon such detection, may cause the transfer arm 18 to move from left to right in FIG. 1, thus automatically moving the reagent strip 14 from the receiving area 12 to the inspection area located within the housing portion 16. The spectrophotometer 10 includes a visual display 23 for displaying various messages relating to the operation of the spectrophotometer 10.

Figure 4:
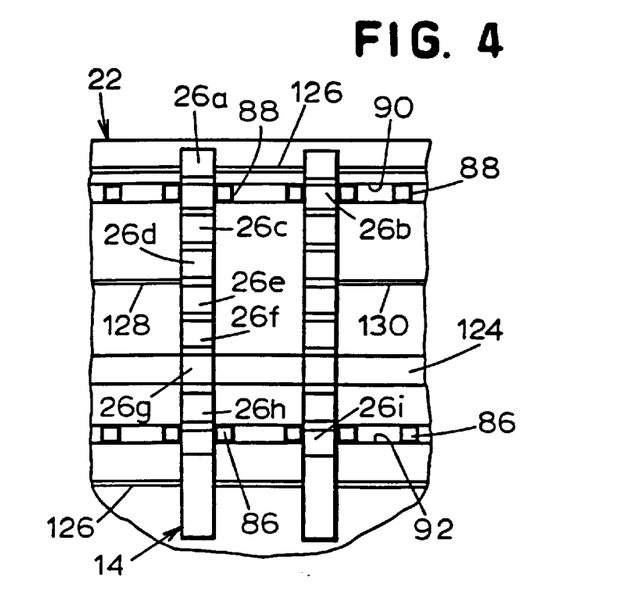
FIG. 4 is a top view of a portion of a reagent strip support shown in FIGS. 1, 7A and 7B.
Figure 6:
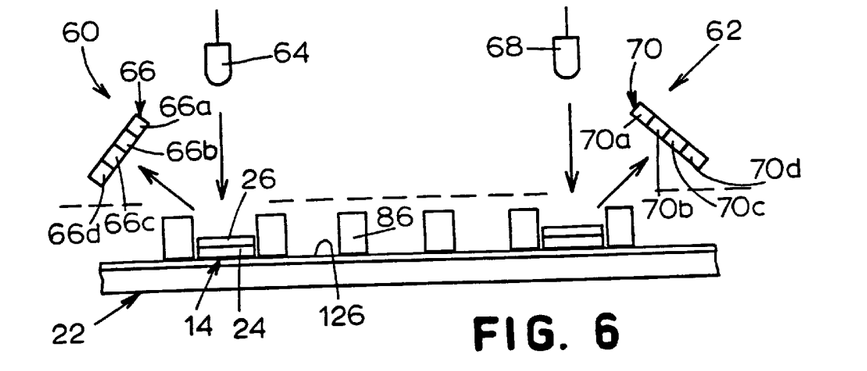
FIG. 6 is a schematic view of a portion of the spectrophotometer.

As shown in FIGS. 4 and 6, the reagent strips 14 used in the spectrophotometer 10 have a thin, non-reactive substrate 24 on which a number of reagent pads 26 are fixed. Each reagent pad 26 may be composed of a relatively absorbent material impregnated with a respective reagent, each reagent and reagent pad 26 being associated with a particular test to be performed. When urinalysis tests are performed, they may include, for example, a test for leukocytes in the urine, a test of the pH of the urine, a test for blood in the urine, etc. When each reagent pad 26 comes into contact with a urine sample, the pad may change color over a time period, depending on the reagent used and the characteristics of the urine sample. The reagent strip 14 may be, for example, a Multistix® reagent strip commercially available from Bayer Corporation.

One of the reagent pads 26 is impregnated with a reagent that causes a color to form in the presence of "occult blood," which as is well known in the art, is defined as relatively small concentrations of blood which are not visible to the naked eye. As used herein, the reference to "occult blood reagent pad" means a reagent pad which is designed to detect occult blood.

Figure 2:
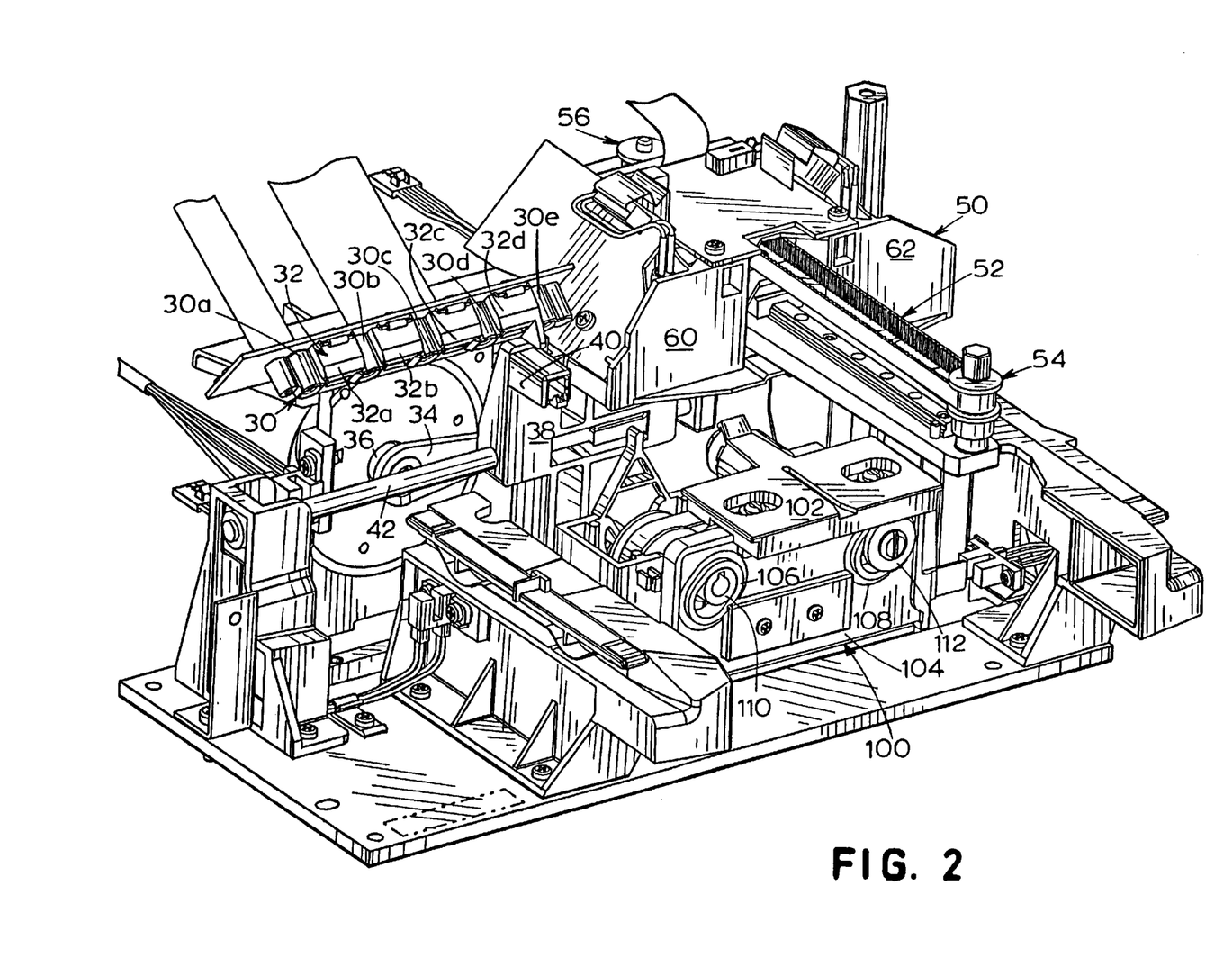
FIG. 2 is a perspective view of an internal mechanical portion of the spectrophotometer of FIG. 1.

FIG. 2 is a perspective view of one embodiment of the interior mechanical structure of the spectrophotometer 10. Referring to FIG. 2, the spectrophotometer 10 may include a light emitting apparatus 30, which may be provided in the form of five light-emitting diodes (LEDs) 30a–30e, which may be in the form of narrow angle, high output LEDs commercially available from Hewlett Packard. The LEDs 30a–30e may be spaced apart so that each of them illuminates a separate portion of the reagent strip receiving area 12. The spectrophotometer 10 may include a detecting apparatus 32, which may be in the form of four light detectors 32a–32d, each of which is disposed between two of the LEDs 30a–30e. The detectors 32a–32d are positioned so that they detect light which is received from portions of the receiving area 12 which are illuminated by the LEDs 30a–30e so that the presence of a reagent strip 14 in the receiving area 12 may be automatically detected (based on the differentiation of a lightly colored reagent strip 14 from the darker color of the spectrophotometer 10).

Alternatively, instead of providing the light emitting apparatus 30 and the light detecting apparatus 32 to automatically detect a reagent strip 14 and move the transfer arm 18 in response thereto, the movement of the transfer arm 18 could be manually initiated by pressing a button (not shown).

As shown in the left-hand portion of FIG. 2, the spectrophotometer 10 includes a pivot arm 34 having a central portion which is connected to a rotatable shaft 36, which is controllably driven by a motor (not shown). The end of the pivot arm 34 is slidably disposed in a vertical shaft formed in the back of a transfer arm support member 38 to which the transfer arm 18 (FIG. 1) is connected. The transfer arm support member 38, which has a receptacle 40 in which an end of the transfer arm 18 is disposed, is slidably supported by a horizontally disposed cylindrical rod 42. The horizontal position and movement of the transfer arm 18 are controlled by selectively causing the pivot arm 34 to rotate about the central shaft 36 to change the lateral position of the end of the pivot arm 34, and thus the lateral position of the transfer arm support member 38.

As shown in the right-hand portion of FIG. 2, the spectrophotometer 10 has a movable carriage 50 that is fixed to one side of a positioning belt 52 supported by a pair of toothed gears 54, 56. The gear 56 is fixed to a rotatable drive shaft (not shown) that is controllably driven by a motor (not shown) to precisely move and position the movable carriage 50 in a direction parallel to the length of the reagent strip 14 (FIG. 1).

The movable carriage 50 has a pair of readheads 60, 62. As shown in FIG. 6, the readhead 60 includes a light source in the form of an incandescent lamp 64 and a detector 66, which may be in the form of four light detectors 66a–66d, each of which is adapted to detect light of a different wavelength, such as red, blue, green and infrared light, for example. The readhead 62 includes a light source in the form of an incandescent lamp 68 and a detector 70, which may be in the form of four light detectors 70a–70d, each of which is also adapted to detect light of a different wavelength. Although the readheads 60, 62 could be designed as disclosed in U.S. Pat. No. 5,661,563 to Howard, et al., which is incorporated by reference herein, no particular design of the readheads 60, 62 is considered necessary to the invention. Alternatively, only a single readhead could be used to optically inspect reagent strips. Any type of detectors 66, 70 could be used, including detectors that detect only a single wavelength of light.

Figure 3:
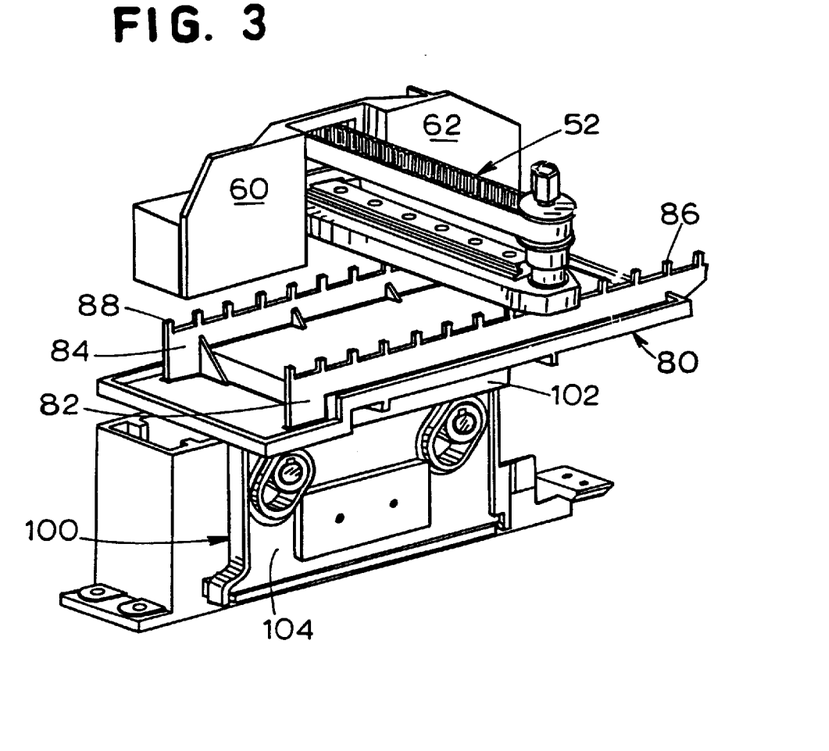
FIG. 3 is a perspective view of an internal mechanical portion of the spectrophotometer of FIG. 1.

FIG. 3 is a perspective view of a portion of the spectrophotometer 10 which shows a reagent strip advancing tray 80. The advancing tray 80 has a pair of upwardly extending walls 82, 84. The upper portion of the wall 82 has a plurality of pegs 86 extending therefrom, and the upper portion of the wall 84 has a plurality of pegs 88 extending therefrom. The pegs 86, 88 are spaced apart by a distance slightly greater than the width of the reagent strips 14 so that the space between each adjacent pair of pegs 86, 88 can accommodate one of the reagent strips 14. Referring to FIG. 4, the pegs 86, 88 of the advancing tray 80 extend upwardly through a pair of slots 90, 92 formed in the reagent strip support table 22.

The reagent strip advancing tray 80 is supported by a positioning mechanism 100 which is shown in FIGS. 2 and 3. The positioning mechanism 100 has a support table 102 which supports the reagent strip advancing tray 80 and a mechanism for moving the support table 102 in a generally circular path which includes a vertical member 104 having a pair of oblong slots 106, 108 formed therein and a pair of motor-driven actuators 110, 112 disposed within the slots 106, 108. Rotation of the actuators 110, 112 causes the vertical member 104 and the support table 102 to move in a circular path, as disclosed in U.S. Pat. No. 4,689,202, which is incorporated by reference herein.

The movement of the support table 102 causes the advancing tray 80 to move in a circular path, which in turn moves the pegs 86, 88 to cause the reagent strips 14 disposed between them to be periodically moved or indexed rightward through the spectrophotometer 10, so that a reagent strip 14 is disposed at a first reagent strip inspection position beneath the readhead 60, and then is disposed at a second reagent strip inspection position beneath the readhead 62.

Referring to FIG. 4, when the advancing tray 80 moves in a single circular path, the pegs 86, 88 move from left to right while they extend upwardly through the reagent strip support table 22, thus moving each of the reagent strips 14 one reagent strip position to the right. During the latter half of the circular motion, the pegs 86, 88 are downwardly retracted so that their upper ends are disposed beneath the upper surface of the support table 22, so that they can be moved from right to left without moving the reagent strips 14. The particular design of the system for conveying the reagent strips 14 from the receiving area 12 to the inspection area within the housing portion 16 and for conveying the reagent strips 14 within the inspection area is not considered necessary to the invention, and other types of conveyor systems could be utilized.

Figure 7A:
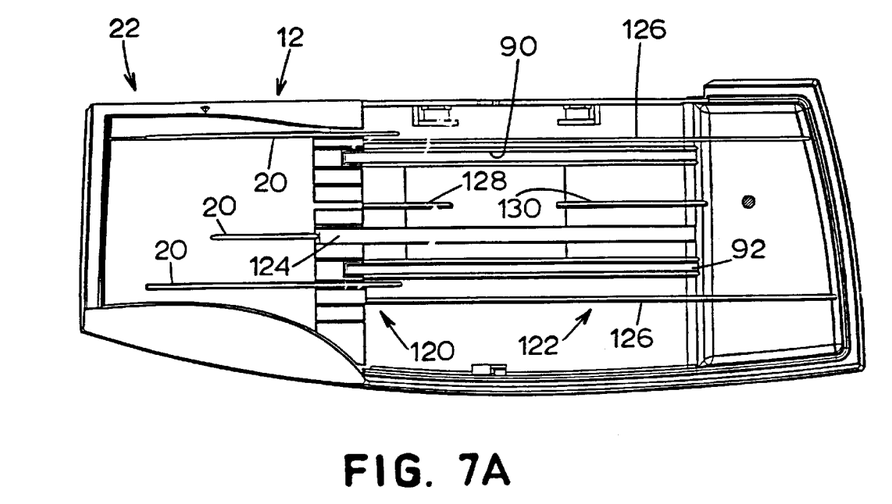
FIGS. 7A and 7B illustrate a reagent strip support.
Figure 7B:
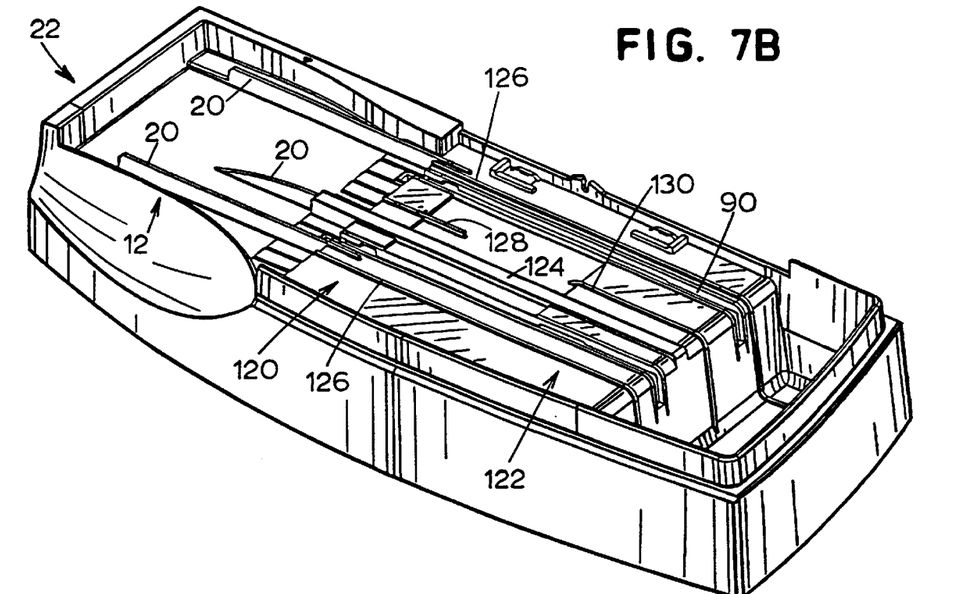

FIG. 7A is a top view of the reagent strip support table 22 shown in FIG. 1, and FIG. 7B is a perspective view of the support table 22. Referring to FIGS. 7A and 7B, the support table 22 has a first inspection position 120 at which a reagent strip 14 (FIG. 4) is disposed when being optically inspected by the readhead 60 (FIG. 6) and a second inspection position 122 at which a reagent strip 14 is disposed when being optically inspected by the readhead 62 (FIG. 6).

When a reagent strip 14 is pushed from the receiving area 12 (by the transfer arm 18) towards the first inspection position 120, the reagent strip 14 makes physical contact with, and is supported above the upper surface of the support table 22 by the ribs 20 and an elongate guide rail 124. The guide rail 124 may be used to maintain the transverse position of reagent strips 14 as they are moved across the support table 22, which position may be maintained due to the fact that the lower surface of the reagent strip substrate 24, which is damp or wet due to the body fluid sample, tends to adhere to the upper surface of the guide rail 124, thus inhibiting movement transverse to the direction of movement (parallel to the ribs 126) of the reagent strip 14.

When the reagent strip 14 is positioned at the first inspection location 120, the reagent strip 14 makes physical contact with, and is supported above the upper surface of the support table 22 by, the ribs 20, the guide rail 124, a pair of outer ribs 126, and an inner rib 128. When the reagent strip 14 is positioned at the second inspection location 122, the reagent strip 14 makes physical contact with, and is supported above the upper surface of the support table 22 by, the outer ribs 126, the guide rail 124, and an inner rib 130.

The reagent strip support table 22 is specially designed to prevent or minimize carryover of body fluid from one reagent strip 14 to the next. That is accomplished in part by minimizing the areas of the support table 22 that come into physical contact with the portions of the reagent strip 14 adjacent a reagent pad 26.

Referring to FIG. 4, as a reagent strip 14 is pushed so that it slides across the support table 22 from left to right in FIG. 4, body fluid on the reagent strip substrate 24 (see FIG. 6) may be left behind on top of the guide rail 124 and the ribs 126, 128, 130. When a subsequent reagent strip 14 follows the same path, the body fluid left behind by the preceding reagent strip 14 may come into contact with the leading (righthand) side edge of the substrate 24 of the subsequent reagent trip 14, and may build up on the subsequent reagent strip 14 so that the body fluid comes into contact with one or more of he reagent pads 26 on the subsequent reagent strip 14.

The reagent pads 26 disposed on a reagent strip 14 are not uniformly affected by carryover of body fluid from one reagent strip 14 to another. Since the occult blood reagent pad is particularly sensitive to such body fluid carryover, the reagent strip support table 22 is designed so that the area on the reagent strip 14 adjacent the occult blood reagent pad does not come into physical contact with the support table 22. Consequently, the likelihood that the portion of a reagent strip 14 which carries the occult blood reagent pad 26 will come into contact with body fluid left by a previously inspected reagent strip 14, as described above, is minimized or eliminated.

Referring to FIG. 4, ten possible positions 26a–26i are shown for an occult blood reagent pad 26 (there is typically one occult blood reagent pad per reagent strip 14). It is considered undesirable for the occult blood reagent pad 26 to occupy the positions 26a, 26b, 26g, and 26i since the reagent strip substrate 24 underneath those positions would come into contact with the rib 126, the pegs 88, the guide rail 124, and the pegs 86, respectively. For example, if the occult blood reagent pad were located in position 26a, body fluid left on top of the rib 126 from a previously inspected reagent strip 14 could contact the leading side edge of the next reagent strip substrate 24 and "climb" onto, or be absorbed into, through the substrate 24, the occult blood reagent pad at that location 26a, thus contaminating the occult blood reagent pad.

Figure 8:
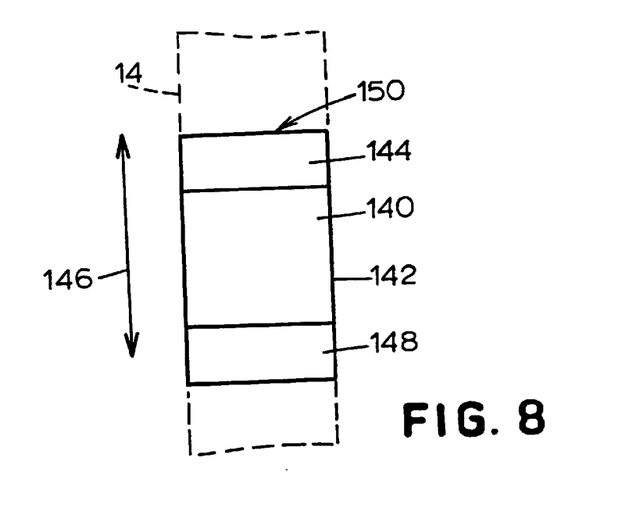
FIG. 8 illustrates a no-contact area on a reagent strip.

FIG. 8 illustrates a plurality of predefined areas of a reagent strip 14. Referring to FIG. 8, the reagent strip 14 has a reagent pad area 140 which is defined as the area on the reagent strip substrate 24 bounded by the perimeter 142 of an occult blood reagent pad. The reagent pad area 140 has a first area 144 adjacent to it which extends for a predetermined distance, such as about one-fourth or about one-eighth of an inch, from the reagent pad area 140 in a first direction parallel to the longitudinal direction 146 in which the reagent pads 26 of the reagent strip 14 are disposed and a second area 148 adjacent to the reagent pad area 140 which extends for a predetermined distance, such as about one-fourth or about one-eighth of an inch, from the reagent pad area 140 in a second direction parallel to the longitudinal 146 of the reagent strip 14. The combined areas 140, 144, 148 may be referred to as a no-contact area 150.

Preferably, during movement of a reagent strip 14 along the reagent strip support 22, to minimize or eliminate body fluid carryover from one reagent strip 14 to another, there is no significant physical contact between the reagent pad area 140 and the reagent strip support 22. This would be the case, for example, where the occult blood reagent pad 26 is located in one of the positions 26c, 26d, 26e, 26f, or 26h.

Alternatively, there may be no physical contact between the no-contact area 150 and the reagent strip support 22. This would be the case (depending on the size of areas 144, 148 of the no-contact area 150) where the occult blood reagent pad is located in the position 26c.

The width of the ribs 126, 128, 130 that support the reagent strips 14 is preferably minimized so as the minimize the likelihood of physical contact between the ribs 126, 128, 130 with either the reagent pad area 140 or the no-contact area 150. The width of the ribs 126, 128, 130 could be, for example, no greater than about one-half the distance between adjacent reagent pads 26.

As shown in FIGS. 4, 7A and 7B, the ribs 128, 130 only extend part way across the reagent strip support 22. That is to further reduce the likelihood of physical contact between the ribs 128, 130 and the reagent pad area 140 and the no-contact area 150. For example, if the occult blood reagent pad is located in the position 26d shown in FIG. 4, there would be no physical contact with the ribs 128, 130 if the reagent strip 14 is properly aligned parallel to its longitudinal axis, as shown in FIG. 4 (because the ribs 128, 130 only contact the area between the adjacent positions 26d and 26e).

However, there can be some movement or misalignment of reagent strips 14 in a direction parallel to their longitudinal axis. For example, due to such misalignment, a reagent strip 14 could be positioned so that the reagent pad area 140 slightly overlaps the ribs 128, 130 (which is not considered to be significant physical contact). In such a case, the fact that the ribs 128, 130 do not extend all the way across the reagent strip support 22 minimizes the likelihood that such strip misalignment will result in significant body fluid carryover. Depending upon the stiffness of the reagent strips 14, it may be preferable that the ribs 128, 130 not be eliminated altogether since they provide support to the center of the reagent strips 14 at the first and second inspection locations 120, 122, and since it may be desirable to have all the reagent pads 26 of a reagent strip 14 spaced equally from the readheads 60, 62.

In the above description, the possible placement of an occult blood reagent pad in one of a number of possible positions 26a–26i has been described. However, it should be noted that the design of the reagent strip support 22, including where the ribs 126, 128, 130 and the guide rail 124 (if present) are placed, may be done in the context of a number of preexisting reagent strip designs. In particular, there may be (for example) four different types of reagent strips 14 intended to be used in the spectrophotometer 10, with each type of reagent strip 14 having the occult blood reagent pad in a different one of the locations 26a–26i. In that case, the guide rail 124 and the ribs 126, 128, 130 could be placed to minimize fluid carryover. For example, the guide rail 124 should be positioned so that it never overlaps the position of an occult blood reagent pad and the ribs 126, 128, 130 should be placed so that they are positioned within the spaces between adjacent reagent pads 26.

Figure 5:
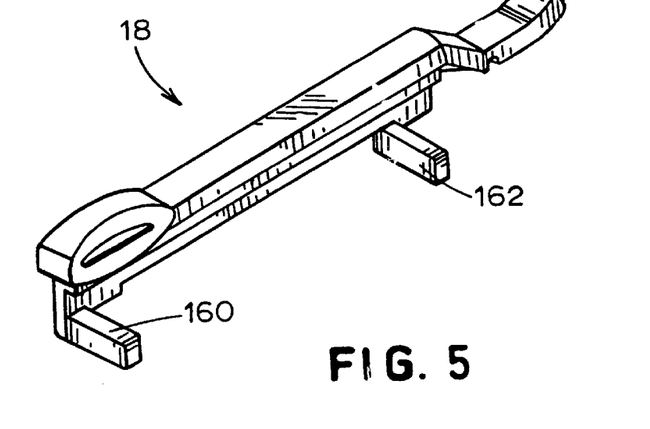
FIG. 5 is a perspective view of a reagent strip transfer arm.

FIG. 5 is a perspective view of the transfer arm 18 shown in FIG. 1. Referring to FIG. 5, the transfer arm 18 has a pair of pusher members 160, 162 which extend laterally from a bottom portion of the transfer arm 18 to make contact with the trailing elongate side edge of each of the reagent strips 14 when the transfer arm 18 pushes the reagent strips 14 from the receiving location 12 of the reagent strip support 22 towards the inspection location 120 of the reagent strip support 22. Each of the pusher members 160, 162 makes contact with the side edges of the reagent strips 14 at the ends of the reagent strips 14 so that the occult blood reagent pad 26 on each of the reagent strips 14 is disposed between the pusher members 160, 162 and so that neither of the pusher members 160, 162 makes contact with the portion of the reagent strip 14 at which the occult blood reagent pad is located or with the no-contact area 150. The transfer arm 18 has no capillaries or other features that are adapted or designed to extract or remove body fluid from the reagent strips 14.

It should be appreciated that the approach to avoiding carryover of body fluid from one reagent strip 14 to another in accordance with the invention is based on minimizing or eliminating physical contact between the reagent pad area 140 and the reagent strip support 22, while not attempting to remove or extract body fluid from the reagent strips 14. In particular, the reagent strip support 22, the pegs 86, 88, the transfer arm 18, and other features of the spectrophotometer 10 are adapted or designed to not remove body fluid from the reagent strips 14. This approach is contrary to prior art approaches which are designed to remove excess body fluid from the reagent strips 14.

Numerous modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed and sought to be secured by Letters Patent is:

1. An apparatus adapted to inspect reagent strips having liquid samples disposed thereon and to reduce contamination of one of said liquid samples with another of said liquid samples, said apparatus comprising:

a reagent strip support (22) adapted to support a reagent strip (14) having a plurality of reagent pads (26) disposed in a longitudinal direction along said reagent strip (14), one of said reagent pads (26) having a reagent sensitive to contamination, said one reagent pad (26) being located at a reagent pad area (140) on said reagent strip (14), said reagent pad area (140) being defined by a perimeter of said one reagent pad (26);

a reagent strip mover (18 and/or 80) adapted to cause said reagent strip (14) to be moved in a direction generally transverse to said longitudinal direction from an initial reagent strip location to an inspection location (120 or 122);

a light emitter (64 or 68) adapted to illuminate said reagent strip (14) when said reagent strip (14) is supported by said reagent strip support (22) at said inspection location (120 or 122); and a detector (66 or 70) adapted to receive light from said reagent strip (14) when said reagent strip (14) is being illuminated by said light emitter (64 or 68), said reagent strip support (22) being adapted to support said reagent strip (14) so that there is no significant physical contact between said reagent strip support (22) and said reagent pad area (140) of said reagent strip (14) when said reagent strip (14) is located at said inspection location (120 or 122) and when said reagent strip (14) is moved between said initial reagent strip location and said inspection location (120 or 122) to reduce the likelihood of carryover of liquid sample from one reagent strip (14) to another.

2. An apparatus as defined in claim 1 wherein said reagent strip mover (18 and/or 80) has a first portion that makes physical contact with said reagent strip (14) at a first point along said reagent strip (14), wherein said reagent strip mover (18 and/or 80) has a second portion that makes physical contact with said reagent strip (14) at a second point along said reagent strip (14), and wherein said reagent pad area (140) of said reagent strip (14) is disposed between said first and second points along said reagent strip (14).

3. An apparatus as defined in claim 1 wherein said reagent strip mover (18 and/or 80) does not make physical contact with said reagent pad area (140) of said reagent strip (14).

4. An apparatus as defined in claim 1 wherein said reagent strip support (22) has a first upwardly extending elongated rib (126, 128 or 130) which makes physical contact with said reagent strip (14) at a first contact point between said reagent pad area (140) and a first end of said reagent strip (14) and a second upwardly extending elongate rib (126, 128 or 130) which makes physical contact with said reagent strip (14) at a second contact point between said reagent pad area (140) and a second end of said reagent strip (14).

5. An apparatus as defined in claim 1 additionally comprising a reagent strip pusher arm (18) which is adapted to push said reagent strip (14) along said reagent strip support (22) while said reagent strip (14) is being supported by said reagent strip support (22), said reagent strip pusher arm (18) being shaped so that no portion of said reagent strip pusher arm (18) makes contact with said reagent pad area (140) of said reagent strip (14).

6. An apparatus adapted to inspect reagent strips having body fluid samples disposed thereon and to reduce contamination of one of said body fluid samples with another of said body fluid samples, said apparatus comprising:

a reagent strip support (22) adapted to support a reagent strip (14) having a plurality of reagent pads (26) disposed in a longitudinal direction along said reagent strip (14), one of said reagent pads (26) being located at a reagent pad area (140) on said reagent strip (14), said reagent pad area (140) being defined by a perimeter of said one reagent pad (26);

a reagent strip mover (18 and/or 80) adapted to cause said reagent strip (14) to be moved in a direction generally transverse to said longitudinal direction from an initial reagent strip location to an inspection location (120 or 122);

a light emitter (64 or 68) adapted to illuminate said reagent strip (14) when said reagent strip (14) is supported by said reagent strip support (22) at said inspection location (120 or 122); and a detector (66 or 70) adapted to receive light from said reagent strip (14) when said reagent strip (14) is being illuminated by said light emitter (64 or 68), said reagent strip support (22) being adapted to support said reagent strip (14) so that there is no physical contact between said reagent strip support (22) and a no-contact area (150) when said reagent strip (14) is located at said inspection location (120 or 122) and when said reagent strip (14) is moved between said initial reagent strip location and said inspection location (120 or 122), said no-contact area (150) being defined as the combined area of said reagent pad area (140), a first area (144) extending at least about one-eighth of an inch from said reagent pad area (140) in a first direction parallel to said longitudinal direction, and a second area (148) extending at least about one-eighth of an inch from said reagent pad area (140) in a second direction parallel to said longitudinal direction, said second direction being opposite said first direction.

7. An apparatus as defined in claim 6 wherein said reagent strip mover (18 and/or 80) has a first portion that makes physical contact with said reagent strip (14) at a first point along said reagent strip (14), wherein said reagent strip mover has a second portion that makes physical contact with said reagent strip (14) at a second point along said reagent strip (14), and wherein said no-contact area (150) of said reagent strip (14) is disposed between said first and second points along said reagent strip (14).

8. An apparatus as defined in claim 6 wherein said reagent strip mover (18 and/or 80) does not make physical contact with said no-contact area (150) of said reagent strip (14).

9. An apparatus as defined in claim 6 wherein said reagent strip support (22) has a first upwardly extending elongate rib (1216, 128 or 130) which makes physical contact with said reagent strip (14) at a first contact point between said no-contact area (150) and a first end of said reagent strip (14) and a second upwardly extending elongate rib (126, 128 or 130) which makes physical contact with said reagent strip (14) at a second contact point between said no-contact area (150) and a second end of said reagent strip (14).

10. An apparatus as defined in claim 6 additionally comprising a reagent strip pusher arm (18) which is adapted to push said reagent strip (14) along said reagent strip support (22) while said reagent strip (14) is being supported by said reagent strip support (22), said reagent strip pusher arm (18) being shaped so that no portion of said reagent strip pusher arm (18) makes contact with said no-contact area (150) of said reagent strip (14).

11. An apparatus adapted to inspect reagent strips having body fluid samples disposed thereon and to reduce contamination of one of said body fluid samples with another of said body fluid samples, said apparatus comprising:

a reagent strip support (22) adapted to support a reagent strip (14) having a plurality of reagent pads (26) disposed in a longitudinal direction along said reagent strip (14), said reagent strip (14) having a body fluid disposed thereon;

a reagent strip mover (18 and/or 80) adapted to cause said reagent strip (14) to be moved in a direction generally transverse to said longitudinal direction from an initial reagent strip location to an inspection location (120 or 122);

a light emitter (64 or 68) adapted to illuminate said reagent strip (14) when said reagent strip (14) is supported by said reagent strip support (22) at said inspection location (120 or 122); and a detector (66 or 70) adapted to receive light from said reagent strip (14) when said reagent strip (14) is being illuminated by said light emitter (64 or 68), said reagent strip support (22) and said reagent strip mover (18 and/or 80) being adapted to not remove said body fluid from said reagent strip (14), wherein one of said reagent pads is located at a reagent pad area on said reagent strip, wherein said reagent pad area is defined by a perimeter of said one reagent pad, and wherein said reagent strip support is adapted to support said reagent strip so that there is no significant physical contact between said reagent strip support and a no-contact area when said reagent strip is located at said inspection location and when said reagent strip is moved between said initial reagent strip location and said inspection location, said no-contact area being defined as the combined area of said reagent pad area, a first area extending at least about one eighth of an inch from said reagent pad area in a first direction parallel to said longitudinal direction, and a second area extending at least about one eighth of an inch from said reagent pad area in a second direction parallel to said longitudinal direction, said second direction being opposite said first direction.

12. An apparatus as defined in claim 11 wherein said reagent strip mover (18 and/or 80) has a first portion that makes physical contact with said reagent strip (14) at a first point along said reagent strip (14), wherein said reagent strip mover (18 and/or 80) has a second portion that makes physical contact with said reagent strip (14) at a second point along said reagent strip (14), and wherein said no-contact area (150) of said reagent strip (14) is disposed between said first and second points along said reagent strip (14).

13. An apparatus as defined in claim 11 wherein said reagent strip mover (18 and/or 80) does not make physical contact with said no-contact area (150) of said reagent strip (14).

14. An apparatus as defined in claim 11 wherein said reagent strip support (22) has a first upwardly extending elongate rib (126, 128 or 130) which makes physical contact with said reagent strip (14) at a first contact point between said no-contact area (150) and a first end of said reagent strip (14) and a second upwardly extending elongate rib (126, 128 or 130) which makes physical contact with said reagent strip (14) at a second contact point between said no-contact area (150) and a second end of said reagent strip (14).

15. An apparatus as defined in claim 11 additionally comprising a reagent strip pusher arm (18) which is adapted to push said reagent strip (14) along said reagent strip support (22) while said reagent strip (14) is being supported by said reagent strip support (22), said reagent strip pusher arm (18) being shaped so that no portion of said reagent strip pusher arm (18) makes contact with said no-contact area (150) of said reagent strip (14).

16. An apparatus adapted to inspect reagent strips having body fluid samples disposed thereon and to reduce contamination of one of said body fluid samples with another of said body fluid samples, said apparatus comprising:

a reagent strip support (22) adapted to support a reagent strip (14) having a plurality of reagent pads (26) disposed in a longitudinal direction along said reagent strip (14), one of said reagent pads (26) having a reagent which enables detection of occult blood and being located at a reagent pad area (140) on said reagent strip (14), said reagent strip (14) having a body fluid disposed thereon;

a reagent strip mover (18 and/or 80) adapted to cause said reagent strip (14) to be moved in a direction generally transverse to said longitudinal direction from a first inspection location (120) to a second inspection location (122);

a light emitter (64 or 68) adapted to illuminate said reagent strip (14) when said reagent strip (14) is supported by said reagent strip support (22) at one of said inspection locations (120 or 122); and a detector (66 or 70) adapted to receive light from said reagent strip (14) when said reagent strip (14) is being illuminated by said light emitter (64 or 68), said reagent strip support (22) being adapted to support said reagent strip (14) so that there is no significant physical contact between said reagent strip support (22) and said reagent pad area (140) when said reagent strip (14) is located between said first inspection location (120) and said second inspection location (122).

17. An apparatus as defined in claim 16 wherein said reagent strip support (22) and said reagent strip mover (18 and/or 80) are adapted to not remove said body fluid from said reagent strip (14).

* * * * *